United States Patent [19]
Fritz

[11] Patent Number: 4,953,974
[45] Date of Patent: Sep. 4, 1990

[54] OPTICAL MEASUREMENT OF THIN FILMS

[75] Inventor: William J. Fritz, Florissant, Mo.

[73] Assignee: McDonnell Douglas Corporation, Long Beach, Calif.

[21] Appl. No.: 286,297

[22] Filed: Dec. 19, 1988

[51] Int. Cl.$^5$ .................... G01N 21/41; G01N 21/59; G01B 11/06

[52] U.S. Cl. ................................ 356/128; 356/382; 356/432; 372/49

[58] Field of Search ............... 356/382, 357, 128, 135, 356/432, 446; 372/49, 92

[56] References Cited

U.S. PATENT DOCUMENTS

| | | | |
|---|---|---|---|
| 3,744,916 | 7/1973 | Bey et al. | 356/382 |
| 3,846,165 | 11/1974 | Ettenberg et al. | 372/49 |
| 4,828,391 | 5/1989 | Zültzke et al. | 356/382 |

FOREIGN PATENT DOCUMENTS

| | | | |
|---|---|---|---|
| 253476 | 1/1988 | German Democratic Rep. | 356/357 |
| 222707 | 12/1984 | Japan | 356/382 |
| 48801 | 1/1988 | Japan | 356/432 |
| 228035 | 9/1988 | Japan | 356/382 |

OTHER PUBLICATIONS

O. S. Heavens, "Measurement of Optical Constants of Thin Films," in *Physics of Thin Films*, vol. 2, G. Hass and R. Thun, Eds., Academic Press, New York and London, 1964, pp. 193–237.

R. E. Denton, R. D. Campbell, and S. G. Tomlin, "The Determination of the Optical Constants of Thin Films from Measurements of Reflectance and Transmittance at Normal Incidence," J. Phys. D 5, 852, (1972).

R. C. McPherdran, L. C. Botten, D. R. McKenzie, and R. P. Netterfield, "Unambiguous Determination of Optical Constants of Absorbing Films by Reflectance and Transmittance Measurements", Appl. Opt. 23, 1197, (1984).

T. C. Paulick, "Inversion of Normal-Incidence, (R, T) Measurements to Obtain N+ik for Thin Films", Appl. Opt. 25, 562, (1986).

S. L. Bragg and J. D. Kelley, "Atmospheric Water Vapor Absorption at 1.3 μm", Appl. Opt. 26, 506, (1987).

*Primary Examiner*—Richard A. Rosenberger
*Attorney, Agent, or Firm*—George W. Finch; John P. Scholl; Gregory A. Cone

[57] ABSTRACT

Properties of thin films are monitored in real time by measuring the interactions of the light from an injection laser diode with the thin film adjacent to one of the facets of the laser diode by an associated photodetector. Thickness, index of refraction and other properties can be measured as a function of the output power, slope efficiency and threshold current of the laser diode.

6 Claims, 2 Drawing Sheets

THRESHOLD CURRENT ($I_{TH}$) —— 72
SLOPE EFFICIENCY ($\eta$) ······· 74
OPTICAL POWER ($P_O$) ----- 76

OPTICAL MEASUREMENT OF THIN FILMS

BACKGROUND OF THE INVENTION

This invention relates to techniques for the optical measurement of thin films. More particularly, this relates to measurement of optical properties of either solid or fluid thin films by measuring the optical interaction of laser light from an injection laser diode in which the thin film is adjacent to one of the facets of the laser diode.

There are a variety of different ways for measuring the optical properties of a thin film. The most usual property to be measured is thickness. Techniques at present include quartz crystal microbalance, witness, optical monitoring, and electroluminescence. In the quartz crystal microbalance technique, a quartz crystal is placed in the chamber in which the thin film is deposited. The quartz crystal has a particular resonant frequency depending upon the mass of the crystal. As more material is deposited upon the crystal, the frequency of the crystal will change. Thickness can be derived from the change in frequency. In the witness, usually one or more glass flats is exposed to deposition within the deposition chamber for the optical thin film. The glass is then removed from the chamber for measurement. The optical monitoring technique is somewhat related to the witness technique. In optical monitoring a beam of light from a remote object source is directed upon a test flat within the deposition chamber. The reflected/transmitted light from the flat is then measured to determine the thickness of the deposited film. In the electroluminescence technique, a quite different process is used. In a system marketed by the INFICON Company, the mass of the deposited material is determined in its gaseous state prior to deposition within the chamber. The mass is measured by running a current through the gas and measuring the resulting luminescence of the gas. The luminescence measurement in turn is a measurement of the mass of the gas within the chamber. The deposition rate can then be calculated and this in turn will give the thickness of the deposited film. All of these techniques suffer from one or more deficiencies. Some have relative low accuracy in measuring the desired optical property of the thin film. Others require that the deposition process be stopped to make the measurement. And others utilize equipment which is very expensive.

SUMMARY OF THE INVENTION

Thickness and other properties of thin films can be measured by an optical system which comprises of placing the thin film adjacent to one facet of an injection laser diode. The interaction of the light from the laser diode with the thin film is then measured by an associated photodetector and the resulting property of the thin film is calculated in real time. Several different embodiments of this basic concept are possible. In a first embodiment, the thin film is a solid film which is deposited upon the back facet of the laser diode simultaneously with the deposition of the solid film onto the surface of a separate object within the deposition chamber. The output power of the laser diode is measured from the front facet of the laser diode by the associated photodetector and subsequent calculations using the measured output power value in real time determine the thin film property of interest. Variations upon this embodiment are also possible. For example, a plurality of laser diodes and associated photodetectors may be utilized in which each laser diode operates at a slightly different wavelength. The outputs from the various laser diodes can then be statistically averaged to get a more accurate calculation of the property of the thin film. Also, for relatively thick thin films, a plurality of individual laser diodes may be sequentially exposed to the deposition of the thin film. As the thickness of the thin film builds up to a point on an individual laser diode to the extent that the measurements become ambiguous, a succeeding laser diode will be exposed to the deposition of the thin film such that accurate measurements may be resumed.

In a second embodiment, using slope efficiency and threshold current values derived from output power measurements at different thicknesses, the index of refraction and absorption coefficient of the deposited material can be determined.

Although the first and second embodiments deal mostly with the measurements of solid thin films, it is also possible to measure properties (index of refraction, absorption coefficient and concentration) of a fluid thin film utilizing a third embodiment of this invention. In the third embodiment, the fluid thin film is confined within an optically thin cavity disposed between an injection laser diode and an associated photodetector. The optically thin cavity is adjacent to the output facet of the injection laser diode. Normally the cavity will be a planar cavity having one side adjacent and parallel to the output facet of the laser and the opposite side parallel to the first side of the cavity and in optical communication with the photodetector. The sides are designed to be optically transparent to the wavelength of the light produced by the laser diode so as not to interfere with the calculations involving the fluid thin film.

DETAILED DESCRIPTION OF THE INVENTION

Owing to the broad scope of this invention, the following discussion will be organized into separate sections. The first will be the basic technique of measuring a thin film deposited as a solid onto the back facet of the laser diode to determine thickness or on the front facet to determine thickness and optical constants. The next section will extend the technique to thicker solid films and those films which have relatively high absorption coefficient. Finally, the discussion will end with a description of the technique to measure the optical constants and/or concentration of a thin fluid film.

Thin Films

Figures 1, 3, 4, 5, 6:
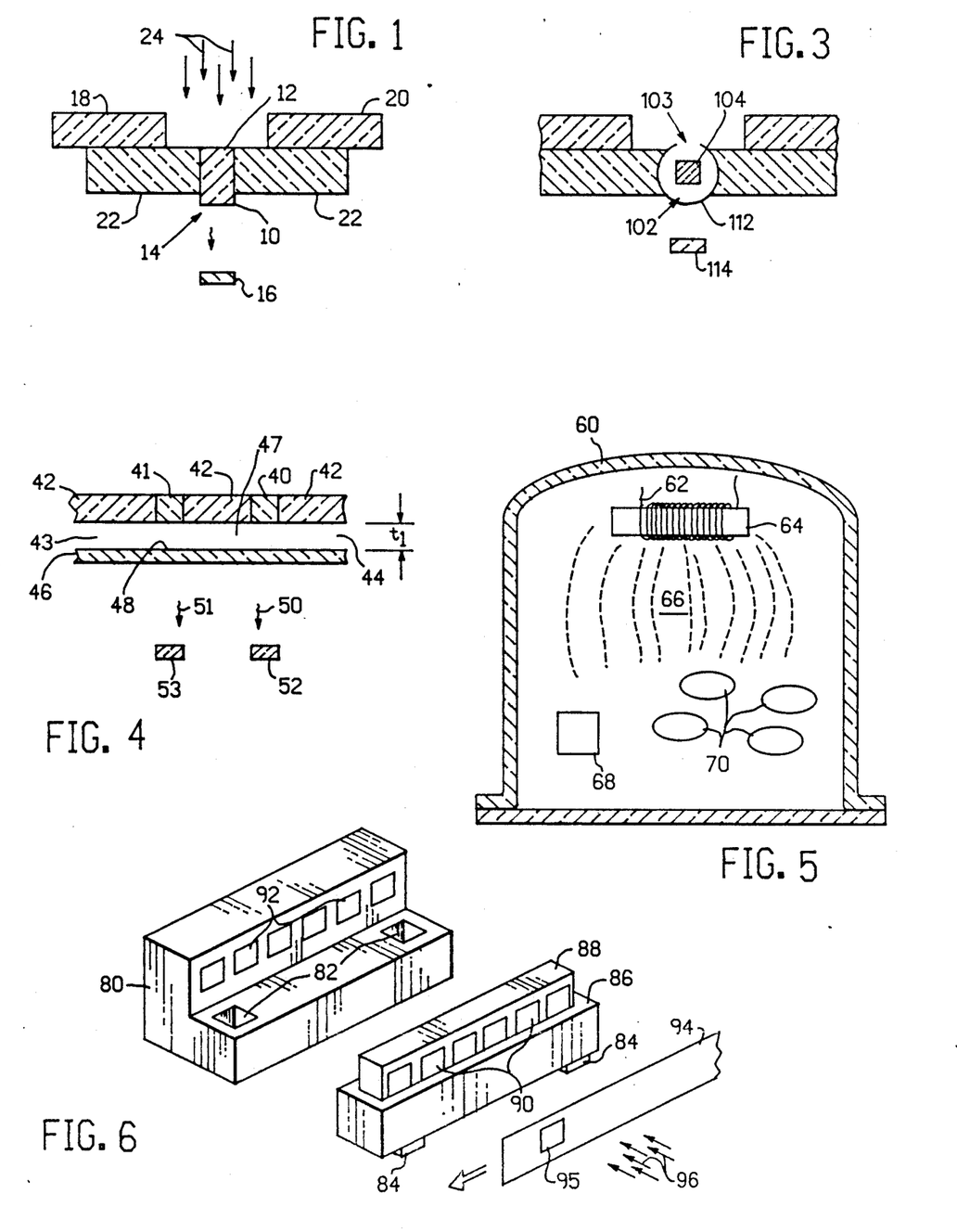
FIG. 1 is a simple schematic view of the system of the first embodiment of this invention involving the thickness measurement of a solid thin film.
FIG. 3 is a simple schematic view of the system of the second embodiment of this invention showing apparatus to measure the thickness, index of refraction and absorption coefficient measurement of a solid thin film.
FIG. 4 is a schematic view showing the cross section of a system designed around the third embodiment of this invention to measure a fluid thin film.
FIG. 5 is a schematic view of a typical deposition chamber set up containing the thickness measurement system of this invention as well as the intended targets for the deposition process.
FIG. 6 is an isometric view of an embodiment employing multiple photodetectors and multiple lasers along with a shutter.

The basic setup for the thickness measurement technique is schematically demonstrated in FIG. 1. This figure illustrates the deposition of a solid film onto the back facet of a laser diode. The deposition of the film material is indicated by the downward pointing arrows 24 which then collect upon the back facet 12 of a laser diode 10. The facet 12 of the laser diode 10 is exposed within an opening whose sides are shown as 18 and 20. In some situations the deposition will be terminated by a shutter means not shown. The laser diode 10 is in turn held by supportinq means 22. The measured light output from the laser diode 10 emanates from the front facet 14. This output light is detected by a photodetector means 16 located a short distance away. In some situations the photodetector will be illuminated directly by the output light from the laser diode 10. But in other situations the photodetector may be eliminated by a fiber optic means not shown or other indirect illumination pathways also not shown. A half wavelength dielectric coating on the back facet and small shutter window may be used for the deposition of metals to prevent shorting of the laser diode. Another configuration would have a thin, replaceable piece of transparent material (e.g., glass flat) interposed between the laser diode 10 and the sides 18 and 20 of the opening.

Turning to a larger scale, FIG. 5 illustrates a typical solid film deposition apparatus. A chamber 60 contains within it a number of objects 70 onto whose upper surfaces the solid film will be deposited. The solid film is created by the evaporation or ionization of a material 64 which in this instance is heated by an electrical coil 62 such that the solid material 64 is vaporized to form the individual particles indicated as 66. These particles then distribute themselves relatively evenly throughout the chamber and coat the upper surfaces of all objects exposed within the chamber. Contained also within the chamber is the laser diode optical measuring device shown as the block 68. As the film is deposited onto the objects 70, it will also be deposited more or less equally upon the upper surface of the laser diode measurement device 68.

Figure 2:
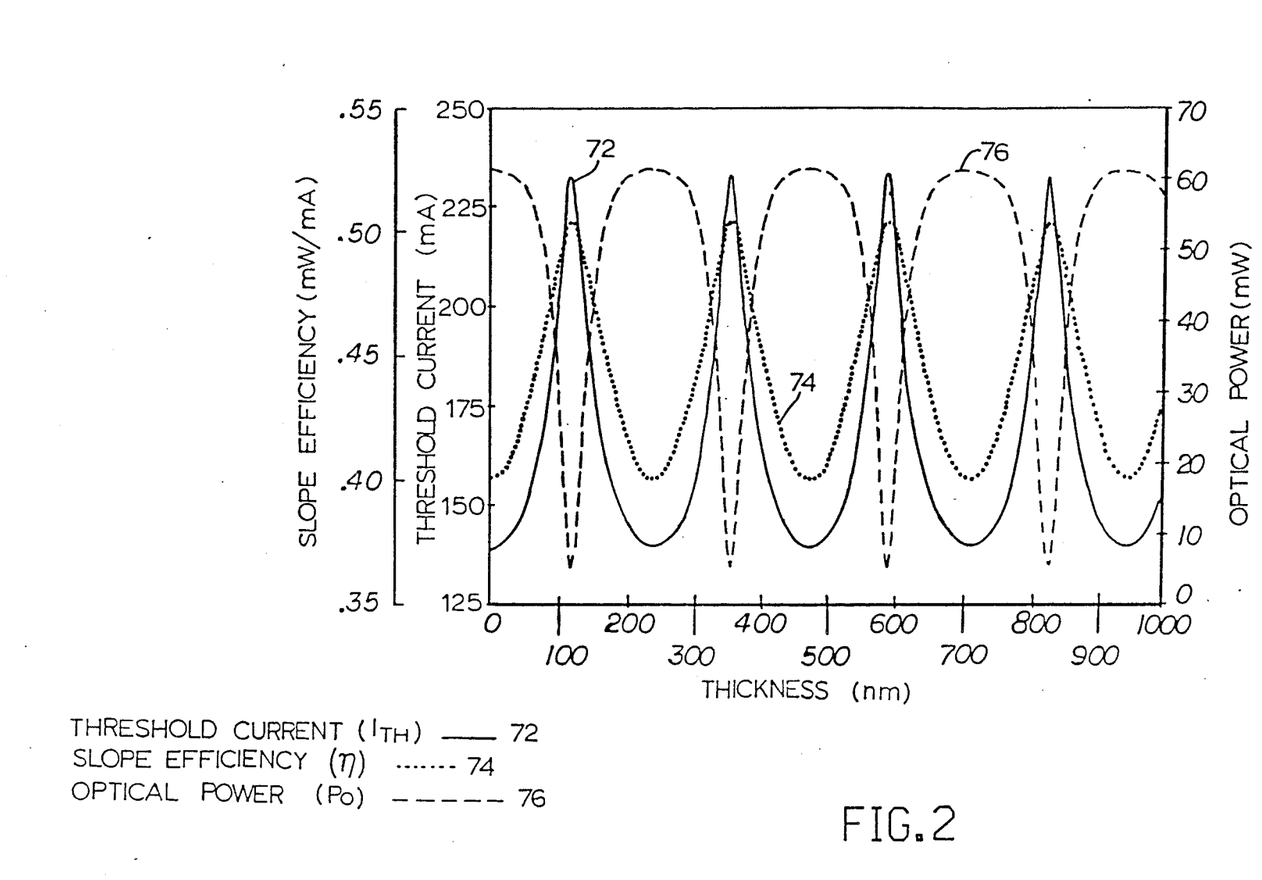
FIG. 2 is a graphical representation of the cyclic interaction of the values for slope efficiency, threshold current, and optical power in relation to the thickness of a thin film.

The reflectivity will change as the film is deposited onto the back facet of the laser diode. The characteristics of the light output from the front facet of the laser diode will change as the reflectivity changes. This occurs in a cyclic fashion which is illustrated in FIG. 2 for a theoretical example.

Solid Thin Films—Thickness Measurement

The thickness of a thin film deposited upon the back facet of the laser diode can be determined by the following technique. The general approach relies on the fact that the output power is a function of the reflectivity of the facets. The reflectivity of a thin film is a function of the index of refraction, absorption coefficient and thickness of the thin film in addition to being a function of the wavelength of the incident light. The reflectivity for a thin film on either facet can be expressed as:

$$R = rr^* = \frac{(r_1)^2 + (r_2)^2 e^{-2\alpha_{ext}t} + 2r_1 r_2 \cos(2\gamma) e^{-\alpha_{ext}t}}{1 + 2r_1 r_2 \cos(2\gamma) e^{-\alpha_{ext}t} + (r_1)^2 (r_2)^2 e^{-2\alpha_{ext}t}} \quad (1)$$

where, $$\gamma = \frac{2\pi n_2 t}{\lambda}, \quad r_1 = \frac{n_2 - n_1}{n_2 + n_1}, \quad r_2 = \frac{n_3 - n_2}{n_3 + n_2}$$

with $n_1$, $n_2$ and $n_3$ being the appropriate indices of refraction for AlGaAs, thin film, and air, respectively, and $\alpha_{ext}$ being the absorption coefficient of the film of thickness t.

Consequently, if the index of refraction and absorption coefficient of the deposited material and wavelength of light emitted by the laser diode are known, then the reflectivity is only a function of the deposited thickness. All of the following, including this approach, assumes normal incidence of the emitted light, minimal scattering of light in the film, single polarization and that the wavelength remains fixed as the reflectivity changes. While in practice these assumptions will not be strictly met, calibration procedures can be utilized if sufficient accuracy is not obtained.

The mathematics of the technique are explained below. The output power ($P_{out}$), the slope efficiency $\eta$, and the threshold current ($I_{th}$) are described in terms of the fundamental properties of a semiconductor laser in equations (2), (3) and (4) below.

$$P_{out} = \left(1 + \left(\frac{R_1}{R_2}\right)^{\frac{1}{2}} \left(\frac{1 - R_2}{1 - R_1}\right)\right)^{-1} \eta(I - I_{th})(V_g), \quad (2)$$

for $I > I_{th}$ where P is measured from the front facet $$\eta = \eta_i / [1 + 2\eta_{int} L / \ln(1/R_1 R_2)] \quad (3)$$

$$I_{TH} = (LdW/\eta_i)\{(1/\beta)[1/L]\ln(1/R_1 R_2) + \alpha_{int}] + J_1\} \quad (4)$$

where:
$V_g$: band gap voltage of AlGaAs (1.53 v);
$\eta_i$: internal quantum efficiency;
$\alpha_{int}$: internal absorption coefficient of the cavity;
$R_1$: front facet reflectivity (power measured here);
$R_2$: back facet reflectivity (film deposition here);
L: cavity length;
d: active layer thickness;
W: cavity width;
$\beta$: nominal gain coefficient; and
$J_1$: current density at which the gain becomes positive.

The material dependent constants usually come from fabrication documentation from the diode maker.

$\eta_i$ can be determined by measurements on different length lasers from a single wafer; $\alpha_{int}$ can be determined by transmission measurements.

The approximate values for the optical parameters can be obtained as follows:

Using the initially measured values of $\eta$ and $I_{th}$, the laser diode dimensions (d, W, and L) and the established values for material dependent properties, ($\beta$, $J_1$, $R_1$ and $R_2$) solve equations (2) and (3) for $\alpha_{int}$ and $\eta_i$. This is easily done since equations (2) and (3) are linear with respect to $\alpha_{int}$ and $\eta_i$ and can be solved simultaneously.

Note that the measured slope efficiency, $\eta_{meas}$, is for power emitted out of one facet. Consequently, $\eta$ for equations (2) and (3) is obtained from $$[1+(R_1/R_2)^{\frac{1}{2}}(1-R_2)/(1-R_1)]^{-1}\eta_{meas}=\eta.$$

when solving for $\eta_i$ and $\alpha_{int}$.

To determine the thickness of a deposited film as a function of output power, the final slope efficiency and threshold current for all possible thicknesses must be calculated prior to deposition. The only parameter that can change during deposition is $R_2$ since the thin film will not affect the internal laser diode properties (i.e., $\alpha_{int}$, $\eta_i$, $\beta$, and $J_1$ do not change). To determine the value of $R_2$ as a function of thickness, substitute the values for $n_2$, $\alpha_{ext}$ and any specific thickness value, t, of the material to be deposited into equation (1) and calculate the new reflectivity, $R_2$. Using the $\alpha_{int}$ and $\eta_i$ previously determined, substitute these with the new $R_2$ value into equation (4) to determine the threshold current. Substitute the $R_2$ value into equation (3) to determine the slope efficiency value. The output power is then determined by substituting the calculated values of slope efficiency and threshold current into equation (2) resulting in an equation which represents optical output power as a function of thickness (t). Calculating output power for all thicknesses will produce a graph which looks something like curve 76 in FIG. 2.

The actual monitoring is done by placing the package comprising a laser diode and associated photodetector represented in FIG. 1 in the deposition chamber as shown in FIG. 5. As material is deposited on the back facet of the laser diode, the film thickness increases. This causes a change in reflectivity and consequently a change in output power. Using the previously determined equation for the output power of the laser diode as a function of deposited thickness, the thickness can be determined. Referring to the graph, it is important to note that a specific output power does not correspond to a unique thickness. It is necessary to monitor the number of cycles to uniquely determine the thickness. A cycle here means the thickness interval represented between consecutive low extrema from the output power measurement. Also, since the slope of curve 76 (i.e., output power) in FIG. 2 changes with thickness, the sensitivity of the measurement changes. A judicious choice of operating parameters or predeposition can increase the sensitivity by having the thickness measured near a large slope point on the graph. Also, further accuracy can be obtained by using a number of laser diodes emitting at different wavelengths and averaging the results.

This operation would advantageously be adapted to computer control. A software routine would be developed to monitor the fluctuations in the output power, the number of cycles detected, the calculation of the power to thickness conversion, and the like. The only input necessary for this particular calculation would be the index of refraction and absorption coefficients of the deposited material as well as the characteristics of the laser diode itself.

Solid Thin Films—Optical Constants Measurement

In other instances it may be useful to calculate the index of refraction and the absorption coefficient of a thin film. This can be done when measurements of output power are taken at several different thickness values for the thin film. The measurement could either be done using several equivalent but separate laser diodes with different film thickness or by a single laser diode with the thickness increasing over time and measurements made at several intervals.

The basic setup for the measurement technique utilizing a single laser diode is schematically demonstrated in FIG. 3. The setup is similar to the one shown in FIG. 1 where in this case the deposition of the film material is indicated by the downward pointing arrows 100 which then collect upon the front facet 104 of a laser diode 102. The diode 102 is held by a rotatable carrier 112. This carrier has an opening 103 proximate to the front facet 104 of the diode 102. The carrier is rotated on command by a small motor, not shown, to expose the front facet 104 to deposition. The carrier 112 is located beneath an opening whose sides are shown as 106 and 108 and is laterally supported by layer 110. The deposition on the laser diode can be interrupted by a shutter means not shown which would be located between the deposition source (indicated by the arrows 100) and the diode 102. The measured light output from the laser diode emanates from the front facet 104. This output light is detected by a photodetector means 114 located a short distance away after the rotatable carrier 112 has turned so that the opening 103 and the facet 104 now face the photodetector 114. In other situations, the photodetector may be coupled to the facet 104 by a fiber optic means not shown or other indirect illumination pathways, also not shown.

The operation of the setup shown in FIG. 3 to determine the optical constants is as follows. The monitoring is done by placing the package comprising a laser diode and associated photodetector represented in FIG. 3 in the deposition chamber as shown in FIG. 5. The deposition commences and the shutter (not shown in FIG. 3) covering laser diode 102 is opened. After a period of time, the shutter is closed and laser diode 102 is rotated by apparatus 112 to face the photodetector 114. Output power versus current measurements are made. The laser diode 102 is then rotated by apparatus 112 to its original position, and the shutter is reopened. This procedure repeats itself until enough measurements are made to determine the optical constants.

The general approach to determine the optical constants of a deposited film is to determine the reflectance, R, and the transmittance, T, of the thin film by relating those values to measured electro-optic properties of the laser diode. The reflectivity for a thin film is given in equation (1). The transmission of a thin film as a function of thickness, index of refraction and absorption coefficient can be expressed as $$T = tt^* = \frac{n_3}{n_1} \cdot \frac{(1-r_1)^2(1-r_2)^2 e^{-\alpha_{ext}t}}{1 + 2r_1r_2\cos(2\gamma)e^{-\alpha_{ext}t} + (r_1)^2(r_2)^2 e^{-2\alpha_{ext}t}} \quad (6)$$

where, $$\gamma = \frac{2\pi n_2 t}{\lambda}, \quad r_1 = \frac{n_2 - n_1}{n_2 + n_1}, \quad r_2 = \frac{n_3 - n_2}{n_3 + n_2}$$

with $n_1$, $n_2$ and $n_3$ being the appropriate indices of refraction for AlGaAs, thin film, and air, respectively, and $\alpha_{ext}$ being the absorption coefficient of the film of thickness t.

To relate reflectance and transmittance to measured output values of the laser diode, first the net output power out of the front facet is examined and is expressed as:

$$P_{out_{calc}} = (1 - R_1) P_{inc.} = \qquad (7)$$

$$V_g \, \eta_{calc} \, (I - I_{th}) \left[ 1 + \left[ \frac{R_1}{R_2} \right]^{\frac{1}{2}} \left[ \frac{1 - R_2}{1 - R_1} \right] \right]^{-1}$$

where $P_{inc}$ is the power of the light incident on the AlGaAs/thin film interface (at the front facet), and $\eta_{calc}$ is the slope efficiency calculated from equation (3). Also, the power out of the thin film is $$P_{out_{meas.}} = TP_{inc} = V_g \, \eta_{meas} \, (I - I_{th}) \qquad (8)$$

where T is the transmission coefficient (equation 6), $P_{inc}$ is as above, and $\eta_{meas}$ is the measured slope efficiency determined from output power versus current measurements after deposition. Dividing equation (8) by equation (7) results in $$T = \frac{\eta_{meas}}{\eta_{calc}} \left( 1 + \left( \frac{R_1}{R_2} \right)^{\frac{1}{2}} \left( \frac{1 - R_2}{1 - R_1} \right) \right) (1 - R_1). \qquad (9)$$

To determine the optical constants, first $\alpha_i$ and $\eta_i$ must be determined. Using the initially measured values of $\eta$ and $I_{th}$, $\alpha_{int}$ and $\eta_i$ are calculated as previously described for the laser diode.

The optical constants are now determined from the measured data in the following manner. Using the new threshold current values after deposition of the thin film, equation (4) is solved for the new reflectivity $R_1$. Solving this equation for two subsequent depositions (i.e., two different thicknesses, $t_1$ and $t_2$) will typically result in two different $R_1$ values. Then by substituting the appropriate reflectivity $R_1$ into equation (3), the slope efficiency in the expression describing the power out of the laser diode from the facet at the GaAs/thin film interface (equation 7) is calculated for each thickness ($\eta_{calc}$). Substituting the appropriate (i.e., $t_1$ or $t_2$, etc.) measured slope efficiency ($\eta_{meas.}$), the calculated slope efficiency ($\eta_{calc.}$), and $R_1$ and $R_2$ into equation (9) gives the transmission coefficient ($T_{thickness\ i}$, i=1 or 2) at each of the two film thicknesses. Using equations (1) and (6) we then have $$R(n_2, \alpha_{ext}, t_1) = R_{thickness\ 1} \qquad (10)$$

$$T(n_2, \alpha_{ext}, t_1) = T_{thickness\ 1} \qquad (11)$$

$$R(n_2, \alpha_{ext}, t_2) = R_{thickness\ 2} \qquad (12)$$

$$T(n_2, \alpha_{ext}, t_2) = T_{thickness\ 2} \qquad (13)$$

four equations with four unknowns ($n_2$, $\alpha_{ext}$, $t_1$, $t_2$). Since these equations are not linear, a computer routine is necessary to solve for $n_2$, $\alpha_{ext}$, $t_1$ and $t_2$. The following references give more information on the nature of these equations and their solutions: (1) O. S. Heavens, "Measurement of Optical Constants of Thin Films," in *Physics of Thin Films*. Vol 2, G. Hass and R. Thun, Eds., Academic Press, New York and London, 1964, pp 193-237; (2) R. E. Denton, R. D. Campbell, and S. G. Tomlin, "The Determination of the Optical Constants of Thin Films from Measurements of Reflectance and Transmittance at Normal Incidence," J. Phys. D 5, 852 (1972); R. C. McPhedran, L. C. Botten, D. R. McKenzie and R. P. Netterfield, "Unambiguous Determinaton of Optical Constants of Absorbing Films by Reflectance and Transmittance Measurements," App. Opt. 23, 1197 (1984). These references are incorporated by reference herein. Due to the periodic nature of equations (1) and (6), there exists no unique solution for only two measurements (i.e., at two thicknesses). However, numerous measurements significantly reduce the allowable solutions. Furthermore, if the approximate thickness is known (to within $\lambda/2$) as typically is the case, the solution from two measurements will suffice. In this manner, the index of refraction ($n_2$) and the absorption coefficient ($\alpha_{ext}$) can be determined. If the deposited material is unknown, the optical constants can identify the material if they are unique to that material.

In certain situations it may be necessary to determine the index of refraction for thin film materials which have a negligibly small absorption coefficient. The above-described process cannot do this. Instead, the technique now requires at least two different laser diodes that emit light at different wavelengths along with associated photodetectors and a controllable shutter. Typically, two photodetectors would be fabricated onto a mount. The mount would have sockets adjacent to the photodetectors to which replaceable laser diodes could be inserted. The back facets of the individual laser diodes face the deposition direction while the front facets face the photodetectors. A controllable shutter is placed between the back facets and the deposition of the thin film. Deposition would be commenced and the shutter would be open for a period of time. The shutter would be closed and power versus current measurements would be made from the front facets. The shutter would then be reopened for a second period of time. The shutter would again be closed and another set of power versus current measurements would be made.

To determine the index of refraction and thickness, first $\eta_i$ and $\alpha_{int}$ must be determined. By using the initially measured values of slope efficiency and $I_{th}$ (taken prior to deposition of the thin film) and the equations for threshold current and slope efficiency, $\alpha_{int}$ and $\eta_i$ are calculated for each laser diode as previuosly described.

To determine the index of refraction, the following is implemented.

Equation 1 is modified for a non-absorbing thin film of thickness t and is written:

$$R = \frac{(r_1)^2 + (r_2)^2 + 2r_1 r_2 \cos(2\gamma)}{1 + 2r_1 r_2 \cos(2\gamma) + (r_1)^2 (r_2)^2} \qquad (14)$$

where, $$Y = \frac{2\pi n_2 t}{\lambda}, \quad r_1 = \frac{n_2 - n_1}{n_2 + n_1}, \quad r_2 = \frac{n_3 - n_2}{n_3 + n_2}$$

and $\lambda$ is the wavelength of emitted light with $n_1$, $n_2$, and $n_3$, being the appropriate indices of refraction for AlGaAs, thin film, and air, respectively.

Then, using the threshold current values determined after deposition of the thin film, equation (4) is solved for the new reflectivity $R_2$. Solving this equation for each laser diode will result in two different $R_2$ values ($R_{diode\ i}$, i=1 or 2) since they are operating at different wavelengths. This results in the following two equations:

$$R(n_{21}, \lambda_1, t_1) = R_{2\ diode\ 1}, \lambda_1, t_1 \qquad (15)$$

$$R(n_{22}, \lambda_2, t_1) = R_{2\ diode\ 2}, \lambda_2, t_2 \qquad (16)$$

Note that the index of refraction, which is a function of wavelength for the two laser diodes, could be slightly different since the laser diodes are operated at different wavelengths. This difference is indicated in the equations by $n_{21}$ and $n_{22}$.

The two sets of power versus current measurements made for each laser diode during deposition (i.e., after a film of thickness $t_1$ and after the second deposition for a film thickness $t_2$) in this set-up in conjunction with the thin film equation (equation 14) for reflectivity for each laser diode can be used to give the following relations:

$$R(n_{21}, \lambda_1, t_1) = R_{2\ diode\ 1}, \lambda_1, t_1 \quad (17)$$

$$R(n_{22}, \lambda_2, t_1) = R_{2\ diode\ 2}, \lambda_2, t_1 \quad (18)$$

$$R(n_{21}, \lambda_1, t_2) = R_{2\ diode\ 1}, \lambda_1, t_2 \quad (19)$$

$$R(n_{22}, \lambda_2, t_2) = R_{2\ diode\ 2}, \lambda_2, t_2 \quad (20)$$

which are four equations with four unknowns, $n_{22}$, $n_{21}$, $t$, and $t_2$.

The appropriate wavelength ($\lambda_1$ or $\lambda_2$) is substituted into the thin film reflectivity equation [equation (14)] and a computer routine is used to solve for $n_{21}$, $n_{22}$, $t_1$, and $t_2$. Note that the approximate thickness (to within $\lambda/2$) must be known to determine the correct thickness value since there is no unique solution. If the wavelengths are close in value and there is small variation in the index of refraction in that wavelength range, two of the previous four equations [equations (19) and (20)] become redundant (since $n_{21}$ approximately equals $n_{22}$). Consequently, only one measurement is needed and the necessary equations become $$R(n_2, \lambda_1, t_1) = R_{2\ diode\ 1}, \lambda_1 \quad (21)$$

$$R(n_2, \lambda_2, t_1) = R_{2\ diode\ 2}, \lambda_2 \quad (22)$$

which are two equations with two unknowns ($n_2$, $t_1$). A computer routine is used to solve for $n_2$ and $t_1$. Once again, the approximate thickness must be known to determine the correct thickness.

Thick Films

Although the technique discussed in this section is also applicable to the measurement of thin film, it is primarily intended for the measurement of thicker films or films which have a relatively high absorption coefficient. In these situations, the application of the previous process would be ineffective because the absorption of the film would rapidly reach a point where measurements using a single laser diode would become meaningless. This thick film technique sequentially exposes a succession of laser diodes, moving from one to another when the first has an excessive buildup of the film in terms of the accuracy of the measurement. The process is monitored by a computer which keeps track of the film thickness buildup on each of the successive laser diodes and will give an indication when the desired thickness is reached. The basic setup can be seen in the isometric drawing in FIG. 6. Here the plurality of laser diodes 90 are found in an integral laser diode bar 88 which will commonly have from about 30 to about 100 individual laser diodes 90 monolithically fabricated into a bar 88 which in turn was cleaved from an AlGaAs wafer. The bar 88 is attached to a heat sink/mount 86 having prongs 84 which are received into slots 82 found on a separate mount 80 which carries a matching plurality of photodetectors 92. The individual electrical connections for the laser diodes and photodetectors are not shown. Only one of the laser diodes is exposed to the thin film deposition here indicated by the arrows 96. This sequential exposure is accomplished by a moveable shutter means 94, here schematically indicated. Again, the movement of the shutter 94 would be controlled by the computer which controls the entire measurement system. The control algorithms and the motion inducing means for the shutter 94 are not shown. The non illustrated portions of the set-up are well within one of ordinary skill in the art. The use of the plug-in laser diode bar assembly is not necessary but facilitates easy replacement of the diode bar. Another configuration could have a thin, replaceable piece of transparent material interposed between the laser bar 88 and the shutter 94.

The operation of the system would commence with the window 95 in the moveable shutter means being positioned over the first of the plurality of individual laser diodes 90. The window 95 would expose the first laser diode to the deposition of the film 96 onto the back facet of the first laser diode. The computer would monitor the measured output power from the photodetector corresponding to that particular laser diode. A back facet of the individual laser diode will receive the deposition of the thin film. The measured output power from the front facet of the laser diode is a function of the reflectivity. The reflectivity is in turn a function of film thickness, index of refraction, and the absorption coefficient of the film. In this particular technique, as previously described for the single laser diode, it is necessary that both the index of refraction and the absorption coefficient be known for the film of interest. Then, the output power can be related to film thickness in much the same manner as was described in the previous section.

A graph of output power from the front facet versus thickness is generated in the fashion of FIG. 2 as previously described by substituting the known index of refraction ($n_2$) and known absorption coefficient ($\alpha_{ext}$) of the deposited material into equation (1), and then substituting this equation for $R_2$ into equations (3) and (4). By substituting $\eta$ from equation (3), $I_{th}$ from equation (4), $R_2$ from equation (1) and $R_1$ from processing documentation into equation (2), the output power from the front facets is now described as a function of thickness [$P_{out}$:$P_{out}(R_2(t))$]. The measured output power as a function of thickness is cyclic as a consequence of the cosine terms in equation (1). Again, it is important to note that a specific output power does not correspond to a unique thickness. However, if the number of cycles is monitored, the thickness can be uniquely determined.

Up to this point, the process has been quite similar to the thickness measuring technique described in the previous section. Depending upon the material deposited, the film will eventually reach a thickness where there will be little change in reflectivity with increased thickness. This condition is primarily a function of the absorption coefficient of the material. Materials with high absorption coefficients (greater than about $10^5$ cm$^{-1}$), such as most metals, will create a reflective film after a small amount of material has been deposited, such that any continued increase in thickness will not be measurable through changes in reflectivity. To measure thick films of any material, including materials with high absorption coefficients, several laser diodes are sequentially used to monitor the thickness. Utilizing the apparatus portrayed in FIG. 6, the first laser diode is monitored to a predetermined point of thickness deposition. Deposition onto the back facet of the first laser diode is terminated prior to the point at which the thickness buildup begins to significantly degrade the accuracy of the thickness measurement. The shutter is then moved to expose the back facet of the second laser diode. The amount of error introduced by not monitoring the deposition during the brief moment of shutter movement is a function of deposition rate and shutter position time. These parameters can be adjusted to be negligibly small. In the alternative, the deposition could be stopped during shutter repositioning to eliminate this error. This in turn could be done by covering the samples in the deposition chamber as shown in FIG. 5 with their own shutter at the same time the laser measurement is briefly terminated by its own shutter movement.

Once the second laser diode is exposed, the computer again monitors the output current from the photodetector to determine the thickness of deposition upon that laser diode. The process continues as described from the first laser diode to the last until the thickness of the film on each laser diode is summed and the total thickness reaches the desired point. Once the deposition of the total film thickness has been terminated, the remainder of the unexposed individual laser diodes on the bar can be utilized for another process deposition or a new entire laser diode bar assembly can be inserted into the sockets if necessary. Or, the thin, transparent material interposed between the laser bar and shutter can be replaced.

Both this thick film technique and the thin film technique discussed in the previous section can be used to monitor the optical properties of epitaxial films grown by metal organic chemical vapor deposition (MOCVD), molecular beam epitaxy (MBE), or any chemical vapor deposition (CVD). Since the substrate upon which the films are grown in these processes is normally at a higher temperature than a laser diode can be operated, and the crystal orientation between the facet and the substrate will differ in some circumstances, the growth rate on the back facet of the laser diode may differ from the growth rate on the substrate. However, when there is a constant difference between the two, a correction can be accomplished by inserting a calibration factor into the calculations.

Fluid Films

By another embodiment of this basic technique, the optical constants of a fluid, here meaning either a gas or a liquid or a combination of the two, can be made. Knowledge of the optical constants of the fluid in turn will indicate the composition and/or concentration of the fluid. Here the basic apparatus is illustrated in the diagram shown in FIG. 4. As with all of the illustrated embodiments, variations are possible. This configuration, however, comprises two laser diodes 40 and 41 held by support structure 42 with associated photodetectors 52 and 53. There is a conduit 47 through which the fluid can flow with one side of the conduit adjacent to the facets of the laser diodes and the other side 48 parallel to and a distance $t_1$ away from the first side. This distance is made small enough so that the material filling the space will behave as a thin film. Although not shown here, the entire package (photodetectors, laser diodes, and the space between the two) is enclosed in a larger structure having two small, controllable openings on the ends of the structure that allow the fluid to flow through into the region between the numbers 43 and 44. The optical design should ensure that the region between the surface of the film 48 facing the photodetector to the photodetector itself appear to the laser diode as a semi-infinite medium of index of refraction, $n_3$. One possible design would be the use of a half wavelength, non-absorbing glass 46 interposed between the fluid flow region and the photodetectors 52 and 53. Of course, the half wavelength thickness glass 46 would need to vary its thickness for the specific wavelength emitted by either laser diode 40 or laser diode 41 since, for this embodiment, they need to emit light at different wavelengths.

When the fluid conduit passage 47 is opened by controllable shutters, not shown, the fluid flows between the laser diodes and the photodetectors. Power versus current measurements are then made for both laser diodes.

Note that this apparatus could consist of one laser diode or any number of laser diodes. The number of laser diodes depends on several factors such as whether the fluid being measured consists of one component or if it is a mixture.

To determine the concentration for a single component fluid, the general procedure utilizes one laser diode. The procedure is as follows. Begin by calculating the constants $\alpha_{int}$ and $\eta_i$ using the initial measured values (i.e., before the gas/liquid is introduced into the system) of slope efficiency and threshold current as previously discussed. Next the fluid is introduced so that it fills the space between 43 and 44 shown in FIG. 4 and power versus current measurements are made. Using the measured threshold current value (determined from power versus current measurements) after the fluid is introduced, equation (4) is solved for the new reflectivity $R_1$. Then by substituting the reflectivity $R_1$ into equation (3), the slope efficiency ($\eta_{calc}$) in the expression describing the power out of the diode from the front facet at the GaAs/thin film interface [equation (7)] is calculated. Substituting $\eta_{calc}$, $\eta_{meas}$ (from power versus current measurements), $R_1$ and $R_2$ into equation (9) gives the transmission coefficient (T). The above procedure results in the following two equations for emission at a specific wavelength:

$$R(n_2, \alpha_{ext}, t_1) = R_1 \quad (23)$$

$$T(n_2, \alpha_{ext}, t_1) = T \quad (24)$$

where R ($n_2$, $\alpha_{ext}$, $t_1$) is from equation (1) and T ($n_2$, $\alpha_{ext}$, $t_1$) is from equation (6) and $R_1$ and T are the values determined as previously described.

Since $t_1$ is known, equations 23 and 24 can be solved by various methods (a computer routine, references 1–4, etc.) to give $n_2$ and $\alpha_{ext}$.

To determine the concentration for a one component fluid, the equations governing index of refraction and absorption coefficient as a function of concentration are used. As an example, the index of refraction for a one component ideal gas as a function of concentration is $$n = 1 + (n_{ref} - 1)\rho/\rho_{ref} = k\rho \quad (25)$$

where n is the index of refraction, $n_{ref}$ and $\rho$ref are the index of refraction and density measured at established reference points, $K_1$ is a constant containing $n_{ref}$ and $\rho_{ref}$. The density, $\rho$, is related to concentration by $$\rho/M = C \tag{26}$$

where M is the mass of one molecule.

The measured absorption coefficient in a simplified form can be given as $$\alpha_{meas} = (C/C_{max})\alpha = A_1 C \tag{27}$$

where $\alpha$ is the absorption coefficient for the particular species of gas, C is the concentration, $C_{max}$ is the maximum concentration for which $\alpha$ is valid and $A_1$ is a constant containing $C_{max}$ and $\alpha$.

To determine concentration, either equation (25) or (27) can be used by setting equation (25) equal to the measured index of refraction [determined from solutions to equations (23) and (24)] and solving for the density (i.e., concentration) or by setting equation (27) equal to the measured absorption coefficient and solving for concentration. A check on the accuracy of the measurement can be accomplished by comparing the results from one to the other. Further accuracy can be obtained by using a number of laser diodes at different wavelengths and averaging the results.

As mentioned previously, equations (25) and (27) are simplified cases for a gas. If they do not provide sufficient accuracy or are inappropriate (i.e., liquid measurement), then a calibration procedure may be conducted or other already developed relations used to determine index of refraction and the absorption coefficient as a function of concentration. Also, the sensitivity can be increased by operating at a wavelength near an absorption line. However, the relation between concentration, wavelength and absorption becomes more complicated and more development for equation (27) or a calibration procedure may be required. Guidance is provided in Reference 5 which is incorporated herein by reference and is within the ordinary skill in the art (S. L. Bragg and J. D. Kelley, "Atmospheric Water Vapor Absorption at 1.3 μm," Appl Opt. 26, 506 (1987).

To determine the concentrations of individual fluids in a mixture of fluids, the previous procedure is slightly modified. The discussion will deal with two fluids, but with modifications, can deal with any number of components in a mixture.

The apparatus shown in FIG. 4 is used with two laser diodes emitting at different wavelengths. As before, measurements are made to determine $\alpha_1$ and $\eta_1$ for each laser diode before the fluid is introduced into the system. Next, the fluid is introduced and power versus current measurements are made for both laser diodes. Then the reflectivity and transmissivity are determined for each laser diode as previously discussed.

The power versus current measurements made with two laser diodes at different wavelengths results in four expressions with $n_{21}$ and $n_{22}$ the indices of refraction and $\alpha_{ext1}$ and $\alpha_{ext2}$ the absorption coefficients of the fluid at the respective wavelengths $\lambda_1$ and $\lambda_2$. This gives the following four expressions.

$$R(n_{21}, \lambda_1, \alpha_{ext1}, t_1) = R_{1\ diode\ 1}, \lambda_1 \tag{28}$$

$$T(n_{21}, \lambda_1, \alpha_{ext1}, t_1) = T_{1\ diode\ 1}, \lambda_1 \tag{29}$$

$$R(n_{22}, \lambda_2, \alpha_{ext2}, t_1) = R_{1\ diode\ 2}, \lambda_2 \tag{30}$$

$$T(n_{22}, \lambda_2, \alpha_{ext2}, t_1) = T_{diode\ 2}, \lambda_2. \tag{31}$$

Note that $t_1$ is a known and fixed value (set at fabrication of the assembly) and $\lambda_1$ and $\lambda_2$ are known. A computer routine or one of several other methods (References 1-4) are used to solve for $n_{21}$, $n_{22}$, $\alpha_{ext1}$, and $\alpha_{ext2}$.

To determine the concentrations and using an ideal gas mixture as an example, equations (25) and (27) are modified to show index of refraction and absorption as a function of the concentration of both gases.

Equation (25) is changed to:

$$K_1\rho_1 + K_2\rho_2 = n_{21} \tag{32}$$

$$K_3\rho_1 + K_4\rho_2 = n_{22} \tag{33}$$

where $\rho_1$ and $\rho_2$ are the densities of the respective gases, $n_{21}$ and $n_{22}$ the index of refractions of the mixture at a particular wavelength ($\lambda_1$ pr $\lambda_2$), and the constants $K_1$, $K_2$, $K_3$, $K_4$ containing the appropriate $n_{ref}$ and $\rho_{ref}$.

Also, equation (27) is changed to:

$$A_1 C_1 + A_2 C_2 = \alpha_{ext\ 1} \tag{34}$$

$$A_3 C_1 + A_4 C_2 = \alpha_{ext\ 2} \tag{35}$$

where $C_1$ and $C_2$ are the concentrations of the respective gases, $\alpha_{ext\ 1}$ and $\alpha_{ext\ 2}$ the absorption coefficients of the mixture at a particular wavelength ($\lambda_1$ or $\lambda_2$), and the constants $A_1$, $A_2$, $A_3$, $A_4$ containing the appropriate $C_{max}$ and $\alpha$. Note that the wavelength of the second laser diode must be such that the index of refraction and/or absorption coefficient of the mixture are different than for the wavelength of the first laser diode. Equations (32) and (33) are two equations with two unknowns as are equations (34) and (35). Consequently, either set can be solved for the concentrations of the respective gases. One set can be solved and the solutions substituted into the second set for verification. This procedure can be extended for any number M (where M is a positive integer) of components by using M laser diodes at different wavelengths. This will generate M equations with M unknowns (the M unknowns being the concentrations of the respective components of the mixture) in the manner previously discussed. The equations are then solved for the concentrations. For greater accuracy or if equations (32) to (35) are inappropriate, calibration procedures can be conducted or other more developed relations used to determine index of refraction and absorption coefficient as a function of concentration for each component in the mixture.

A variation of this procedure can be used to determine the composition and concentration of an unknown mixture. Using the example of a two component mixture, the procedure follows as previously described to the point where equations (28) to (31) are obtained. Equations (32) and (33) are now used, but the index of refraction (and reference index of refraction and reference density) for two possible fluids in the mixture are used in the constants $K_1$, $K_2$, $K_3$, and $K_4$. The equations are then solved for the concentrations. The concentrations along with the concomitant absorption coefficients for the possible fluids are substituted into equations (34) and (35). If the calculated values agree with the measured values (i.e., measured absorption coefficients), then the gases are identified by the optical constants. A computer routine may be developed to run through all the possible combinations until a solution is obtained. This procedure relies on the optical constants being unique for any given fluid but will not work in the cases were there is ambiguity. Once again, this procedure can be developed for M components by using M laser diodes at different wavelengths as long as each wavelength from the individual laser diodes results in a different measured index of refraction and absorption coefficient. Also, as before, if more accuracy is required or equations (32) to (35) are inappropriate, calibration procedures may be conducted or other relations used that describe concentration as a function of index of refraction and absorption for each component of the mixture.

These embodiments have been presented for the purposes of illustration and should not be considered as limitative. Other variations are possible for practising the invention, whose true scope is to be found in the following claims.

It is claimed:

1. A method to measure a property of a thin film of a fluid in real time comprising;
    confining the fluid within an optically thin cavity of known thickness adjacent one output facet of an injection laser diode having certain operating parameters and material characteristics wherein the output from the facet passes through the cavity and illuminates associated photodetector means such that any solid wall acting to confine the fluid is optically transparent and has a thickness which is an even number of quarter wavelengths of the laser output beam passing therethrough,
    measuring the output power of the injection laser diode with the photodetector means, and
    calculating the property of the thin film of a fluid as a function of the measured output power and the operating parameters and the material characteristics of the laser diode.

2. The method of claim 1 wherein the laser diode is combined with at least one other laser diode, all of slightly different wavelengths, such that all the diodes provide output beams passing through the fluid cavity to the photodetector means wherein the outputs are individually measured at the photodetector means and then statistically averaged to provide the measurement of the property of the thin film.

3. A method for measuring a property of a thin film during deposition of the film onto a surface of an object comprising:
    initiating deposition of a thin film of a material having certain optical properties within an enclosed chamber onto both the surface of the object and also onto the back facets of a plurality of laser diodes, each of which operates at a slightly different wavelength, whose outputs from the front facets are measured by associated photodetector means, and
    measuring the property of the thin film simultaneously with the deposition of the film as a function of the statistically averaged measured output power from the plurality of laser diodes.

4. A method for measuring a property of a thin film during deposition of the film onto a surface of an object comprising:
    initiating deposition of a thin film of a material having certain optical properties within an enclosed chamber onto both the surface of the object and also onto the back facets of at least one set of laser diodes with a plurality of laser diodes, each diode in a set operating at a slightly different wavelength, whose outputs from the front facets are measured by associated photodetector means wherein each of the diodes may be individually and controllably exposed to the deposition by associated shutter means, such that a first set of at least two of the laser diodes is exposed to the deposition at the initiation of the deposition, then the outputs of these diodes are measured until the deposited thickness of the thin film becomes so great as to degrade the accuracy of the measurements from the first set, then simultaneously terminating measurements from the first set and initiating deposition of the thin film onto a second set of at least two laser diodes by the associated shutter means with concurrent initiation of measurement of the outputs from the second set, and then continuing to sequentially expose further sets of the plurality of laser diodes until the measurements of the property are complete, and
    measuring the property of the thin film simultaneously with the deposition o the film as a function of the statistically averaged measured output power from the plurality of laser diodes.

5. The method of claim 4 wherein the property is the thickness of the thin film.

6. A method to measure the index of refraction of a thin film of a fluid in real time comprising:
    confining the fluid within an optically thin cavity disposed between one output facet of an injection laser diodes and associated photodetector,
    measuring the output power of the injection laser diode with the photodetector or photodetectors, and
    calculating the index of refraction of the fluid as a function of the measured output power.

* * * * *